United States Patent
Stoffel et al.

(10) Patent No.: US 8,349,580 B2
(45) Date of Patent: Jan. 8, 2013

(54) METHODS AND KIT FOR PROTEASE ENZYME ASSAYS

(75) Inventors: Joseph J. Stoffel, Hastings, MN (US); Louis C. Haddad, Mendota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/394,353

(22) PCT Filed: Aug. 30, 2010

(86) PCT No.: PCT/US2010/047110
§ 371 (c)(1),
(2), (4) Date: Mar. 6, 2012

(87) PCT Pub. No.: WO2011/031573
PCT Pub. Date: Mar. 17, 2011

(65) Prior Publication Data
US 2012/0164675 A1    Jun. 28, 2012

Related U.S. Application Data

(60) Provisional application No. 61/240,768, filed on Sep. 9, 2009.

(51) Int. Cl.
*C12Q 1/37* (2006.01)
*C12Q 1/00* (2006.01)
*C12N 9/76* (2006.01)
*C12N 9/50* (2006.01)

(52) U.S. Cl. ............. 435/23; 435/219; 435/213; 435/4; 530/350

(58) Field of Classification Search ................ 435/4, 23, 435/213, 219; 530/350
See application file for complete search history.

(56) References Cited

U.S. PATENT DOCUMENTS

| | | | |
|---|---|---|---|
| 3,886,043 A | | 5/1975 | Walker et al. |
| 5,631,127 A | * | 5/1997 | Sundrehagen ............ 435/4 |
| 6,090,541 A | | 7/2000 | Wicks et al. |
| 6,667,388 B2 | | 12/2003 | Bein et al. |
| 7,256,012 B2 | | 8/2007 | Wei et al. |
| 7,410,769 B2 | | 8/2008 | Burroughs-Tencza |
| 2002/0159989 A1 | | 10/2002 | Bein et al. |
| 2005/0211635 A1 | | 9/2005 | Yeh et al. |
| 2009/0053738 A1 | | 2/2009 | Davis et al. |

FOREIGN PATENT DOCUMENTS

| | | |
|---|---|---|
| WO | 02/041000 | 5/2002 |
| WO | 03/025125 | 3/2003 |
| WO | 03/095475 | 11/2003 |
| WO | 03/102544 | 12/2003 |
| WO | 2009/102835 | 8/2009 |
| WO | 2009/134509 | 11/2009 |
| WO | 2011/017325 | 2/2011 |

OTHER PUBLICATIONS

Mungall, B.A. et al.; "Thermolysin Activates Equine Lamellar Hoof Matrix Metalloproteinases"; J. Comp. Path.; vol. 126; 2002; pp. 9-16.
Brochure entitled "ANASPEC-SensoLyte™ 520 MMP Substrate Sampler Kit *Fluorimetric*"; Google; dated Apr. 2, 2009; retrieved from the Internet Feb. 2, 2012; 8 pgs.
Brochure entitled "invitrogen™—Molecular Probes The Handbook—Technical Focus: Fluorescence Resonance Energy transfer (FRET)—Note 1.2"; retrieved from the internet Aug. 19, 2009; 5 pgs.
Brochure entitled "RDT info—Current information on rapid diagnostic tests—Technologies: Lateral-flow-Lateral-flow: how it works"; 2008; PATH; retrieved from the internet Aug. 19, 2009; 2 pgs.
Brochure entitled "RDT info—Current information on rapid diagnostic tests—Technologies: Lateral-flow-Lateral-flow: test components"; 2008; Path; retrieved from the internet Aug. 19, 2009; 5 pgs.
Wikipedia document entitled "Subtilisin"; modified Feb. 24, 2009; retrieved from the internet Jul. 8, 2009; 2 pgs.
Wikipedia document entitled "Matrix metalloproteinase"; modified Mar. 29, 2009; retrieved from the internet Apr. 20, 2009; 7 pgs.
Information from SIGMA-ALDRICH® entitled "Trypzean-Sigma® Product #T3568"; 2009; retrieved from the internet on Jul. 9, 2009; 2 pgs.

* cited by examiner

*Primary Examiner* — Maryam Monshipouri

(57) ABSTRACT

A method for testing efficacy of a protease enzyme assay, the method comprising providing an enzyme which acts as a surrogate enzyme control for the protease enzyme; combining the surrogate enzyme control with an assay substrate for the protease enzyme; and determining a change in the assay substrate resulting from the surrogate enzyme control acting on the assay substrate; wherein the protease enzyme is selected from the group consisting of metalloproteinases, serine proteases, and cysteine proteases; a method for conducting a protease enzyme assay using the method for testing efficacy; a kit including an enzyme which acts as a surrogate enzyme control for a protease enzyme in testing efficacy of a protease enzyme assay; and a method of releasing the kit are provided.

36 Claims, 1 Drawing Sheet

METHODS AND KIT FOR PROTEASE ENZYME ASSAYS

CROSS REFERENCE TO RELATED APPLICATIONS

This application is a 371 of PCT/US10/47110, filed Aug. 30, 2010, which claims priority to U.S. Provisional Patent Application No. 61/240,768, filed on Sep. 9, 2009, which is incorporated herein by reference in its entirety.

BACKGROUND

Commercial assays used in life sciences and research applications are available for measuring the presence and/or activities of some proteases. Certain of these enzymes, such as matrix metalloproteinases (MMPs), are known to have one or more functions associated with wound healing. For example, MMPs may affect cell proliferation, migration, differentiation, angiogenesis, apoptosis, and host defense. As a result, reliably assaying for such enzymes, for example, in wounds, is becoming increasingly relevant.

To assure reliability, laboratory regulations for in vitro diagnostics require the clinic, hospital, or lab to perform a product verification of performance at the site at which the diagnostic will be used.

Accordingly, there is a need for methods and materials useful in verifying the performance of and conducting protease assays.

SUMMARY

The present invention provides a method for testing efficacy of a protease enzyme assay, a method of conducting a protease enzyme assay, a kit which can be used to conduct these methods, and a method of releasing such a kit for use by a practitioner. The methods and kit include a surrogate enzyme control for the protease enzyme. The surrogate enzyme control is used to determine whether or not an assay substrate for the protease enzyme has been compromised prior to the substrate's use in the assay. In certain embodiments, using the surrogate enzyme control in place of the protease enzyme to which the assay is directed eliminates the need for the user to keep and maintain expensive protease enzyme and/or expensive equipment for preserving the protease enzyme.

Accordingly, in one embodiment, there is provided a method for testing efficacy of a protease enzyme assay, the method comprising:
  providing an enzyme which acts as a surrogate enzyme control for a protease enzyme;
  combining the surrogate enzyme control with an assay substrate for the protease enzyme; and
  determining a change in the assay substrate resulting from the surrogate enzyme control acting on the assay substrate;
  wherein the protease enzyme is selected from the group consisting of metalloproteinases, serine proteases, and cysteine proteases.

In another embodiment, there is provided a method for conducting a protease enzyme assay, the method comprising:
  testing efficacy of the protease enzyme assay comprising:
    providing an enzyme which acts as a surrogate enzyme control for a protease enzyme;
    combining the surrogate enzyme control with an assay substrate for the protease enzyme; and
    determining a change in the assay substrate resulting from the surrogate enzyme control acting on the assay substrate; and
  determining a level of the protease enzyme in a biological sample by contacting the assay substrate with at least a portion of the biological sample;
  wherein the protease enzyme is selected from the group consisting of metalloproteinases, serine proteases, and cysteine proteases.

In another embodiment, there is provided a kit including:
  an enzyme which acts as a surrogate enzyme control for a protease enzyme in testing efficacy of a protease enzyme assay comprising a predetermined assay substrate for the protease enzyme;
  a reconstitution buffer; and
  an expected fluorescence range and/or ultra violet or visible light absorbance range of the predetermined assay substrate; wherein the predetermined assay substrate at a specified concentration has a fluorescence or absorbance within the expected fluorescence or absorbance range when acted upon by the surrogate enzyme control at a specified concentration; and/or
  an expected color range or color level range of a binding zone of a flow device when contacted with the predetermined assay substrate; wherein the predetermined assay substrate causes the binding zone of the flow device to exhibit a color or level of color within the expected color range or color level range when the assay substrate is acted upon by the surrogate enzyme control at a specified concentration.

In a further embodiment, there is provided a method of releasing a kit according to the above kit embodiment or any one of the embodiments thereof described herein where the kit includes the expected fluorescence range and/or ultra violet or visible light absorbance range, the method comprising:
  determining the expected fluorescence or absorbance range of the predetermined assay substrate at a specified concentration when acted upon by the surrogate enzyme control at a specified concentration; and
  providing the expected fluorescence or absorbance range for including in the kit.

In a further embodiment, there is provided a method of releasing a kit according to the above kit embodiment or any one of the embodiments thereof described herein where the kit includes the expected color range or color level range of a binding zone of a flow device, the method comprising:
  determining the expected color range or color level range of the binding zone of the lateral flow device when contacted with the predetermined assay substrate acted upon by the surrogate enzyme control at a specified concentration; and
  providing the expected color range or color level range of the binding zone of the lateral flow device for including in the kit.

DEFINITIONS

The term "absorbance" is used herein according to its accepted meaning as defined by Beer's law.

The term "fluorescence", unless otherwise indicated, refers to the fluorescence intensity of the assay substrate when acted upon by a protease enzyme or a surrogate enzyme control minus the fluorescence intensity in the absence of these enzymes. This may be expressed as relative fluorescence units (RFUs).

The expression "acts as a surrogate enzyme control" refers to the surrogate enzyme control acting on the protease enzyme assay substrate in combination with all other required assay components to successfully determine whether or not the substrate and assay components therewith have been compromised and can be used to conduct the protease enzyme assay.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

The above summary of the present invention is not intended to describe each disclosed embodiment or every implementation of the present invention. The description that follows more particularly exemplifies illustrative embodiments.

BRIEF DESCRIPTIONS OF THE FIGURE

DETAILED DESCRIPTION OF ILLUSTRATIVE EMBODIMENTS OF THE INVENTION

Figure 1:
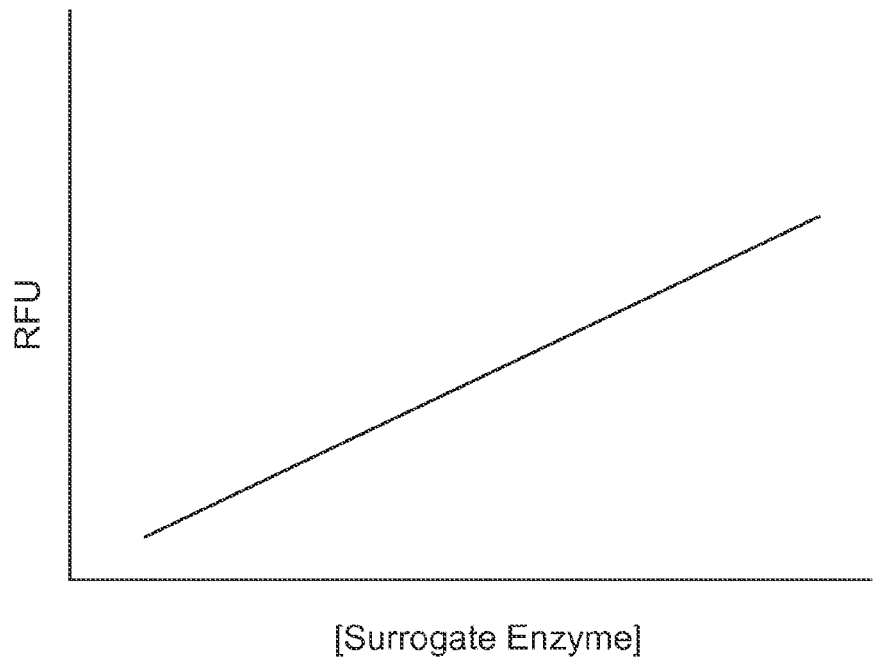
FIG. 1 is a standard plot of fluorescence of a predetermined assay substrate versus surrogate enzyme control concentration.

As indicated above, methods and a kit are now provided which provide for the use of a surrogate enzyme control instead of a target protease enzyme to verify or test the efficacy of a protease enzyme assay, thereby alleviating problems associated with using the protease enzyme or proenzyme thereof for this purpose. Currently, the enzyme being assayed is used as the control. However, it is now recognized that because certain of these enzymes have little or no stability under normal storage conditions, problems arise in using them as enzyme controls for verifying efficacy of the assay. For example, currently marketed MMP assays contain lyophilized proenzyme, which needs to be stored at ultra cold temperatures (e.g., −70° C.) for stability. Such conditions are not routinely available in clinical environments. Moreover, the proenzyme must be activated to form the even less stable active enzyme for use as the control. The compound normally used to activate proenzyme MMPs is 4-aminophenylmercuric acetate (APMA), raising further issues of safe handling and disposal of a mercury-containing material.

A method has now been found in which a thermally stable proteolytic enzyme with broad enzymatic activity can be used as a surrogate enzyme control for the target protease enzyme. The surrogate enzyme control is used to verify efficacy of the protease enzyme assay by demonstrating that the substrate for the protease enzyme used in the assay has not been compromised by shipping and storage, for example, auto-hydrolysis or other degradation routes of the substrate, or has not been otherwise adulterated and is suitable for use by the practitioner.

For certain embodiments, including any one of the above embodiments, preferably the surrogate enzyme control is selected to be used in place of a protease enzyme. For certain of these embodiments, including any one of the above embodiments, preferably the protease enzyme is selected from the group consisting of metalloproteinases, serine proteases, and cysteine proteases. For certain of these embodiments, the protease enzyme is a metalloproteinase or a serine protease. For certain of these embodiments, the protease enzyme is a matrix metalloproteinase. For certain of these embodiments, the surrogate enzyme control is selected from the group consisting of thermolysin, porcine trypsin, bovine trypsin, and recombinant trypsin. Thermolysin (EC 3.4.24.27) is also known as *Bacillus thermoproteolyticus* neutral proteinase. Trypsin (EC 3.4.21.4) is available in various forms including, for example, procine trypsin, bovine trypsin, and recombinant trypsin. Porcine trypsin and bovine trypsin, unless purified, typically include both α and β forms of the trypsin, the β-trypsin normally being the most active. Recombinant trypsin is available under the tradename TrypZean (available from Sigma-Aldrich, St. Louis, Mo.). This is an animal-free bovine trypsin expressed in corn.

Matrix metalloproteinases include, for example, MMP-1, -8, and -13 (collagenases); MMP-2 and -9 (gelatinases); MMP-3, -10, and -11 (stromelysins); MMP-7 and -26 (matrilysin); MMP-12 (metalloelastase); MMP-14, -15, -16, -17, -24, and -25 (membrane-type); MMP-19, -21, -23A, -23B, -27, and -28 (various); and MMP-26 (enamelysin). For certain embodiments, the matrix metalloproteinase is MMP-9.

Metalloproteinases are zinc-dependent and as such are subject to inactivation in the presence of chelators. For certain embodiments, the surrogate enzyme control used in place of a metalloproteinase preferably is a metal cation dependent enzyme. Thermolysin includes a calcium ion at the active site and would, therefore, be similarly subject to inactivation. For certain embodiments, including any one of the above embodiments where the surrogate enzyme control is selected from the group consisting of thermolysin, porcine trypsin, bovine trypsin, and recombinant trypsin, preferably the surrogate enzyme control is thermolysin.

For certain embodiments, the surrogate enzyme controls for serine and cysteine proteases can cleave peptide bonds in substrates which serine and cysteine proteases act upon, respectively. For certain embodiments, including any one of the above embodiments, except where the protease enzyme is a matrix metalloproteinase, the protease enzyme is a serine protease. Serine proteases include a serine residue at the active site. In one example, the serine protease is elastase. For certain embodiments, the surrogate enzyme control acts on the assay substrate with a specificity that is specific to the target serine protease. For certain embodiments, the surrogate enzyme control used in place of a serine protease preferably includes a serine residue at the active site. For certain of these embodiments, the surrogate enzyme control is subtilisin.

For certain embodiments, including any one of the above embodiments, except where the protease enzyme is a matrix metalloproteinase or a serine protease, the protease enzyme is a cysteine protease. Cysteine proteases include a cysteine residue at the active site. In one example, the cysteine protease is a cathepsin. For certain embodiments, the surrogate enzyme control acts on the assay substrate with a specificity that is specific to the target cysteine protease. For certain embodiments, the surrogate enzyme control used in place of a cysteine protease preferably includes a cysteine residue at the active site. For certain of these embodiments, the surrogate enzyme control is papain.

When acted upon by the protease enzyme and by the surrogate enzyme control, the substrates used in the protease assays undergo a detectable, measurable change. For certain embodiments, including any one of the above method embodiments which includes testing efficacy of a protease enzyme assay, determining the change in the assay substrate is carried out by measuring a property of the assay substrate. When testing efficacy of a protease enzyme assay using the surrogate enzyme control, the efficacy of the assay is verified or not verified depending upon whether the measured property falls within or outside a predetermined range. For certain of these embodiments, the property is determined to be within a predetermined range, and the efficacy of the assay is verified. Alternatively, when the assay substrate, including components used with the assay substrate in the assay, has been compromised, such as by degradation on shipping and storage or by adulteration or contamination, for example, by a chelator, quencher, absorber, or the like, the efficacy of the assay would not be verified. For certain of these embodiments, the property is determined to be outside a predetermined range, and the efficacy of the assay is not verified.

Figure 2:
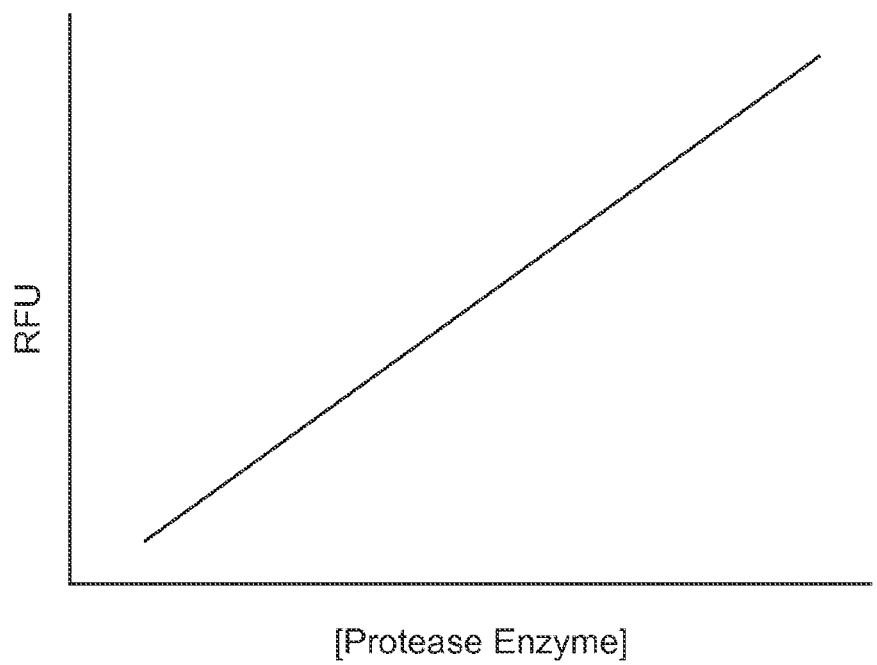
FIG. 2 is a standard plot of fluorescence of a predetermined assay substrate versus protease enzyme concentration.

The predetermined range may be established by measuring the property of the assay substrate as a function of the concentration of the surrogate enzyme control. The results may be plotted as shown, for example, in FIG. 1 wherein the measured property is exemplified as fluorescence in relative fluorescence units (RFU). A range of the measured property can be established as the predetermined range, such that the plot intersects the range at a chosen concentration of surrogate enzyme control. The plot, such as that shown in FIG. 1, should correlate to a plot of the measured property as a function of a target protease concentration. An example of this is shown in FIG. 2 wherein the measured property is exemplified as fluorescence in relative fluorescence units (RFU). In order to correlate, the assay substrate at the same concentration when subjected to a target protease enzyme concentration displays the property at a level measurably different from the property in the absence of the target protease enzyme. For example, when the property is fluorescence, the fluorescence is measurably greater in the presence of the target protease concentration than in its absence. The target protease enzyme concentration is at a level relevant for detecting and/or quantifying the target protease enzyme in a biological sample of interest. The chosen concentration of surrogate enzyme is base, at least in part, on the activity of the particular lot of enzyme, because of purity, conformational, and other possible differences between lots. However, a sufficient concentration of surrogate enzyme is chosen such that the measured property is at a level readily distinguishable from it level in the absence of the enzyme, and which clearly shows that the assay substrate is or is not compromised when either of these is the case.

For certain embodiments, preferably the protease assay substrates are polypeptides labeled with one or more dye groups, at least one of which undergoes a detectable change when the peptide is cleaved. Dye groups which can be used for this purpose are known and described, for example, in U.S. Pat. Nos. 7,256,012 (Wei et al.) and 7,410,769 (Burroughs-Tencza). Some non-limiting examples of dyes which may be used as labels include fluorescein, tetramethylrhodamine, rhodamine B, lissamine, rhodamine X, Texas Red, cyanine dyes, Dabcyl, BODIPY dyes, alexa dyes, QSY 7 and QSY 9 dyes, and other fluorescent dyes commonly available from Invitrogen Corp (Carlsbad, Calif.). Other dyes known to those skilled in the art may also be used.

Briefly, at least one dye group is attached to the protease assay substrate. The dye group may have a visibly observable or optically measurable characteristic. For example, the dye group may have an observable color; the dye group may have an ultra violet or visible light absorbance maximum at a particular wavelength, a level of absorbance at a particular wavelength or wavelength range, certain color coordinate values, or the like, which can be measured by spectrophotometric and/or colorimetric means; or the dye group may emit light at a particular wavelength or wavelength range or at a particular intensity, which can be measured by fluorometric or luminometric means. For certain embodiments, when the protease substrate is intact, the dye group is in sufficient proximity to at least one second group for the second group to modulate the fluorescence and/or absorbance level or spectrum of the dye group. The second group may be, for example, another dye group, a fluorescent energy transfer acceptor, a chromophoric light absorbing compound, or a quencher. Modulation of the fluorescence or light absorbance of the dye group may occur by various mechanisms including, for example, dye dimerization and/or an energy transfer mechanism which may include nonradiative energy transfer, radiative energy transfer, intramolecular resonance energy transfer, and/or the like. When the substrate is cleaved by the protease or the surrogate enzyme control, the modulation is reduced or eliminated, causing a detectable change in the dye group, for example, an optical change such as a change in fluorescence intensity, a change in ultra violet or visible light absorbance, a change in color, a change in intensity of a color, and/or the like.

In one example, the assay substrate is a fluorescence resonance energy transfer (FRET) polypeptide, which contains a fluorescent dye group and a quencher group held in close proximity to the fluorescent dye group while the assay substrate remains intact. Little, if any, light is emitted when the fluorescent dye group is excited, and a low or no signal is measured. When the polypeptide is cleaved by the enzyme, the quencher is separated from the fluorescent dye group, which now emits light when excited, and a signal can be measured. The intensity of the signal is proportional to the amount of substrate cleaved, which in turn is proportional to the amount of active enzyme (the concentration of the substrate being constant). Examples of fluorescent dye groups (donor)/quencher group (acceptor) pairs include: fluorescein/tetramethylrhodamine, IAEDANS/Fluorescein, EDANS/Dabcyl, fluorescein/fluorescein, BODIPY FL/BODIPYFL, Fluorescein/QSY 7 and QSY 9 dyes. For certain embodiments, including any one of the above embodiments where determining the change in the assay substrate is carried out by measuring a property of the assay substrate, the property is fluorescence. For certain of these embodiments, the assay substrate undergoes an increase in fluorescence when acted upon by the protease enzyme and by the surrogate enzyme control. The expression "by the protease enzyme and by the surrogate enzyme" refers to these enzymes acting upon the assay substrate separately and not in combination with each other.

For certain embodiments, including any one of the above embodiments where determining the change in the assay substrate is carried out by measuring a property of the assay substrate, except where the property is fluorescence, the property is ultra violet or visible light absorbance. For certain of these embodiments, the assay substrate undergoes a change in ultra violet or visible absorbance when acted upon by the protease enzyme and by the surrogate enzyme control.

In another example, the assay substrate is a polypeptide with at least two different binding groups attached to the polypeptide and separated from each other by at least one peptide bond susceptible to cleavage by a target protease enzyme. One of the binding groups has a dye or other optically observable or measurable moiety or label associated therewith. For example, one of the binding groups may be biotin and the other binding group may be an antibody or antigen labeled with a dye, colloidal gold, or other optically observable or measurable label. When cleaved by a target protease enzyme a change in the polypeptide (assay substrate) can be determined by observing or measuring a color change or lack of a color change at separate zones (e.g., test line and control line) of a flow device to which the polypeptide has been applied. Bound to one zone of the device is a complementary binding moiety (e.g., avidin/streptavidin) for one binding group (e.g., biotin) and bound to another zone is a complementary binding moiety (e.g., antibody or antigen) for another binding group (e.g., antigen or antibody). In such an example, the biotin-containing portion of the cleaved polypeptide binds to the avidin/sterptavidin zone (test line), and a low or no color change is observed or measured at this zone.

In the above example, the antibody- or antigen-containing portion of the polypeptide, whether cleaved or not cleaved, binds to the antigen or antibody zone (control line), and a color change is observed or measured, thereby showing that assay substrate is present and appropriately observable. For certain embodiments, including any one of the above embodiments where determining the change in the assay substrate is carried out by measuring a property of the assay substrate, except where the property is fluorescence or ultra violet or visible light absorbance of an assay substrate solution or suspension, the property is optically observable or measurable at a binding zone of a flow device. In the above example, the binding zone of the flow device is the test line. For certain of these embodiments, the flow device is a lateral flow device or a vertical flow device, such as a column. For certain of these embodiments, the flow device is preferably a lateral flow device. For certain of these embodiments, the optically measurable property is selected from the group consisting of fluorescence, color, and level of color. For certain of these embodiments, the assay substrate causes the binding zone of a lateral flow device to exhibit a first color or level of color when the assay substrate is acted upon by the protease enzyme and by the surrogate enzyme control, and to exhibit a second color or level of color when the assay substrate is not acted upon by the protease enzyme and by the surrogate enzyme control. The first and second colors are readily distinguished by visual observation or by optical measurement means. The same is true for the first and second levels of color. Color can be measured by well known methods, such as using a colorimeter and obtaining Hunter, CIELAB, or other color coordinates. The level of color can be measure, for example, by determining optical density using a densitometer.

One example of the above described type of binding assay is a protein binding assay using a lateral flow test with an immunologically specific reaction to the substrate, such as described in U.S. Patent Application No. US 2009/0053738 (Davis et al.). Here the lateral flow device has binding zones for different epitopes of the substrate. An intact substrate with a label such as a gold nanoparticle is detectable by a visual color development by both binding zones indicating a negative proteolytic result. When the substrate is acted on by the protease, two substrate fragments are produced with each fragment containing a different epitope for the lateral flow binding zones. Additionally, one fragment contains the label while the other fragment does not. When the substrate acted on by the protease is then placed onto the lateral flow device the substrate fragments bind to their respective zones, however only one zone is visible, thus indicating a positive proteolytic result.

As indicated above, commercial protease assays are available. These assays include a substrate as described above. For example, the SENSOLYTE 520 Assay (available from AnaSpec, Fremont, Calif.) includes an MMP substrate, which is a FRET polypeptide. In another example, a colorimetric elastase specific substrate (available from Calbiochem) is used. Here the visible light absorbance of the substrate changes as the target elastase or the surrogate enzyme control acts on the substrate. Other examples of commercial protease assays include FLUOROKINE E MMP Activity Kits (available from R&D Systems, UK), CHEMICON MMP Gelatinase Activity Kit, (available from Chemicon International, Billerica, Mass.), Human Neutrophil Elastase ELISA Kit (available from Hycult Biotechnology, The Netherlands).

Protease assays which have been tested for efficacy as described herein can be used to determine the presence and/or amount of a protease enzyme in a biological sample. For certain embodiments, including any one of the above embodiments which includes determining a level of the protease enzyme in a biological sample, the biological sample is selected from the group consisting of animal tissues, wound fluids, body fluids, saliva, tears, urine, blood serum, and blood plasma. For certain of these embodiments, the biological sample is a wound fluid, blood serum, blood plasma, or a combination thereof. Biological samples may be collected using known methods and devices. The biological samples may be used as collected or modified using known dilution, separation, and/or purification methods. For certain embodiments, preferably at least a portion of the biological sample or modified sample is combined with a solution of the assay substrate, preferably with mixing, thereby contacting the assay substrate with the sample.

As indicated above, the kit described herein includes a surrogate enzyme control. Preferably, this enzyme is provided in a form which does not require special storage conditions other than room temperature or readily available moderate refrigeration. For certain embodiments, preferably this enzyme is provided in a dry form, for example, as a lyophilized composition, and packaged to exclude moisture.

The kit described herein also includes a reconstitution buffer for re-dissolving the surrogate enzyme control and bringing the enzyme to a specified concentration. For certain embodiments, preferably the reconstitution buffer is non-interfering (e.g., non- chelating, non-quenching, etc.), colorless, stable, and other than a primary amine. Examples of useful buffers include phosphate buffers, pyrophosphate buffers, carbonate buffers, and Good's buffers. Examples of Good's buffers include ACES, ADA disodium, ADA, BES, BES sodium, BICINE, BIS TRIS hydrochloride, BIS-TRIs propane, BIS-TRIS, CAPS, CAPSO sodium, CAPS CHES, DIPSO, EPPS, HEPBS, HEPES, HEPES sodium, HEPES potassium, HEPES sodium hdyrate, HEPPSO hydrate, MES hemisodium, MES, MES potassium MES sodium, MES, MOBS, MOPS hemisodium, MOPS sodium, MOPS, MOPSO sodium, MOPSO, PIPES dipotassium, PIPES disodium, PIPES sequisodium, PIPES sodium, PIPES, POPSO sesquisodium, POPSO, TABS, TAPS sodium, TAPS, TAPSO sodium, TAPSO, TES sodium, TES, and TRICINE. The specified concentration is the concentration of enzyme required to act on the assay substrate, such that a measurable property of the substrate, for example, fluorescence or absorbance, is within an expected range in response to the enzyme acting on the substrate.

The kit described herein further includes an expected fluorescence or ultra violet or visible light absorbance range of a predetermined assay substrate, and/or an expected color range or color level range of a binding zone of a flow device when contacted with the predetermined assay substrate when the surrogate enzyme control at a specified concentration acts upon the substrate, also at a specified concentration. The kit may include a plurality of expected fluorescence or absorbance ranges of a plurality of predetermined assay substrates, and/or a plurality of expected color ranges or color level ranges of binding zones of flow devices. This allows the kit to be used for testing and verifying (or not verifying) the efficacy of a plurality of protease enzyme assays. For certain embodiments, including any one of the above kit embodiments, having a fluorescence or ultra violet or visible light absorbance within the expected fluorescence or absorbance range indicates that the predetermined assay substrate is verified for use in assaying the protease enzyme. For certain embodiments, including any one of the above kit embodiments, the binding zone of the flow device exhibiting a color or level of color within the expected color range or color level range indicates that the predetermined assay substrate is verified for use in assaying the protease enzyme. The predetermined assay substrate is any enzyme substrate used in a protease enzyme assay for which the surrogate enzyme control is to be used to test efficacy of the assay.

The kit described herein may be used not only for testing efficacy of a protease enzyme assay, but may also include protease enzyme assay components, making the kit useful for also conducting a protease enzyme assay. Accordingly, for certain embodiments, including any one of the above kit embodiments, the kit further comprises the predetermined assay substrate. The substrate may be provided in dry form or in a solution. The solution may include a buffer or a buffer may be included in the kit for reconstituting the substrate provided in dry form. After verifying the efficacy of the substrate, the assay can be carried out on a biological sample.

Certain devices for use in conducting a protease enzyme assay may also be included in the kit. Accordingly, for certain embodiments, including any one of the above kit embodiments, the kit further comprises a device for assaying the protease enzyme. For certain of these embodiments, the device is selected from the group consisting of a sampling tool, a sample receptacle, a reconstitution chamber, an assay chamber, a readout chamber, a lateral flow device, a device which incorporates a combination of or all of the foregoing, and a combination thereof.

For certain embodiments, including any one of the above kit embodiments which includes the predetermined assay substrate, the predetermined assay substrate is contained by the device. For example, the substrate may be contained by the sampling tool, which can be used to collect a biological sample and bring the substrate in contact with the biological sample. In another example, the substrate may be contained by a lateral flow device to which a biological sample can be applied. The biological sample may then be brought into contact with the substrate at the same time or after application of a lateral flow of the sample, the substrate, or both.

For certain embodiments, including any one of the above embodiments, the kit further comprises a sampling tool. Examples of useful sampling tools include QUICK SWAB (available from Medical Packaging Corp., Camarillo, Calif.), CLEANTRAC and AQUATRAC (available from Biotrac, UK), sample acquisition devices such as those described in International Application Nos. PCT/US2009/033638 and PCT/US2009/033869 and in copending application entitled "SAMPLING DEVICES AND METHODS OF USE," U.S. Ser. No. 61/231,236, filed Aug. 4, 2009, and the like.

For certain embodiments, including any one of the above kit embodiments, the predetermined assay substrate undergoes an increase in fluorescence when acted upon by the surrogate enzyme control (and by the target protease enzyme). For certain of these embodiments, the kit includes the expected fluorescence range of the predetermined assay substrate. In use according to one example, the fluorescence of a solution of the predetermined assay substrate, which is the substrate of a protease enzyme assay to be tested for efficacy, is measured absent the surrogate enzyme control (first fluorescence value). The surrogate enzyme control is then added to the substrate solution at a specified concentration, and the fluorescence of the resulting solution is measured (second fluorescence value). The first fluorescence value may be subtracted from the second fluorescence value to arrive at the enzyme derived fluorescence of the substrate. Alternatively, when the first fluorescence value is determined, the fluorometer is adjusted to record zero fluorescence, such that the second fluorescence value is a direct reading of the enzyme derived fluorescence of the substrate. When the enzyme derived fluorescence is within the expected fluorescence range provided by the kit, the assay substrate is verified for use in assaying the target protease enzyme.

Alternatively, for certain embodiments, including any one of the above kit embodiments, the predetermined assay substrate undergoes a change in ultra violet or visible light absorbance when acted upon by the surrogate enzyme control (and by the target protease enzyme). For certain of these embodiments, the kit includes the expected absorbance range of the predetermined assay substrate. In this case, in use according to one example, the ultra violet or visible light absorbance at a particular wavelength of a solution of the predetermined assay substrate, which is the substrate of a protease enzyme assay to be tested for efficacy, is measured absent the surrogate enzyme control (first absorbance value). The surrogate enzyme control is then added to the substrate solution at a specified concentration, and the absorbance of the resulting solution is measured (second absorbance value). The first absorbance value may be subtracted from the second absorbance value to arrive at the enzyme derived absorbance of the substrate. Alternatively, when the first absorbance value is determined, the spectrophotometer is adjusted to record zero absorbance, such that the second absorbance value is a direct reading of the enzyme derived absorbance of the substrate. When the enzyme derived absorbance is within the expected absorbance range provided by the kit, the assay substrate is verified for use in assaying the target protease enzyme.

Alternatively, for certain embodiments, including any one of the above kit embodiments, the predetermined assay substrate causes the binding zone of a lateral flow device to exhibit a first color or level of color when the assay substrate is acted upon by the surrogate enzyme control, and to exhibit a second color or level of color when the assay substrate is not acted upon by the surrogate enzyme control. For certain of these embodiments, the kit includes the expected color range or color level range of the binding zone of the lateral flow device when contacted with the predetermined assay substrate acted upon by the surrogate enzyme control.

As indicated above, there is also provided a method of releasing a kit according to any one of the above kit embodiments where the predetermined assay substrate undergoes a change in fluorescence or ultra violet or visible light absorbance when acted upon by the surrogate enzyme control, the method comprising determining the expected fluorescence or ultra violet or visible light absorbance range of the predetermined assay substrate at a specified concentration when acted upon by the surrogate enzyme control at a specified concentration; and providing the expected fluorescence or absorbance range for including in the kit. One or both of these ranges may be provided in printed form or in a machine readable form. The expected fluorescence range is the range of possible fluorescence, such as RFU, at a particular wavelength of emission or range of wavelengths of emission from the uncompromised substrate in response to the surrogate enzyme control acting on the substrate. The fluorescence range is outside of the wavelength or range of wavelengths used for excitation. Since some variability in enzyme activity and substrate emission is expected, a range of possible fluorescence intensities is provided with the kit.

The expected ultra violet or visible light absorbance range is the range of possible absorbance values at a particular wavelength of absorbance or range of wavelengths of absorbance by the substrate in response to the surrogate enzyme control acting on the substrate. Because some variability in enzyme activity and substrate absorbance is expected, a range of possible absorbance values is provided with the kit.

For certain embodiments, the method of releasing a kit further comprises measuring the fluorescence or ultra violet or visible light absorbance of the predetermined assay substrate at the specified concentration in combination with the protease enzyme at at least one concentration; and determining if the measured fluorescence or absorbance fits a standard plot of fluorescence or absorbance of the predetermined assay substrate versus protease enzyme concentration. FIG. 2 illustrates an example of such a standard plot. When the fluorescence or absorbance fits the standard plot, the substrate is known to be uncompromised. A fit may be considered to exist when the fluorescence or absorbance is within an acceptable range of the standard plot.

There is also provided a method of releasing a kit of any one of the above kit embodiments where the kit includes the expected color range or color level range of the binding zone of the lateral flow device when contacted with the predetermined assay substrate acted upon by the surrogate enzyme control, the method comprising determining the expected color range or color level range of the binding zone of the lateral flow device when contacted with the predetermined assay substrate acted upon by the surrogate enzyme control at a specified concentration; and providing the expected color range or color level range of the binding zone of the lateral flow device for including in the kit. One or both of these ranges may be provided as a visual sample, in printed form, or in a machine readable form (e.g., color coordinates, optical density, or the like). The expected color range or color level range is the range of possible colors or color levels exhibited by the binding zone of a lateral flow device when contacted by uncompromised substrate acted on by the surrogate enzyme control. Since some variability in enzyme activity and substrate color development when bound to the binding zone is expected, a range of possible colors or color levels is provided with the kit. Typically, the color range and color level are similar to that of the binding zone of the flow device when no substrate binds to this zone, since uncompromised substrate is effectively cleaved by the surrogate enzyme control, and the portion of the cleaved substrate which binds to the binding zone lacks a dye group. At the same time, at least one other binding zone binds the other portion of the cleaved substrate which is labeled with a dye group, and this other binding zone develops a color or level of color much different than the prior to contact with this portion of the substrate. Accordingly, for certain embodiments, the kit may also include an expected color or color level range for this other binding zone or control zone.

The temperature at which the above described enzymatic reactions between substrate and enzyme are carried out is normally at 20 to 40° C. and for certain embodiments, preferably at 25 to 37° C.

Objects and advantages of this invention are further illustrated by the following examples, but the particular materials and amounts thereof recited in these examples, as well as other conditions and details, should not be construed to unduly limit this invention.

EXAMPLES

The following examples are a Fluorescent Resonance Energy Transfer (FRET) peptide assay which contains a fluorophore and a corresponding quencher linked together by the enzyme substrate. Once the substrate is cleaved by the enzyme the fluorophore is detached from the quencher and will no longer be able to inhibit the fluorophore. Thus the fluorophore will emit light when excited and the signal can be measured. The intensity of the signal is proportional to the amount of enzyme activity and substrate cleaved.

Enzyme activity curves were generated using the SENSOLYTE 520 Generic MMP Assay Kit commercially available from AnaSpec Corporation of San Jose, Calif. Included in the SENSOLYTE kit is a 5-FAM/QXL 520 FRET peptide as a MMP substrate.

Comparative MMP-9 Examples

Pro-MMP-9 (Human recombinant, AnaSpec catalogue No. 72009) and active MMP-9 (Human recombinant, 83 kDa Gelatinase Gelatinase B, commercially available from Calbiochem as catalogue No. PF024; Calbiochem is a brand of EMD Chemicals Inc., an affiliate of Merck KGaA of Darmstadt, Germany) were used as the comparator enzymes. Each of these two MMP-9 enzymes was diluted with "Component D" the assay buffer, provided in the SENSOLYTE kit, to the concentrations listed in Table 1 below. The pro-MMP-9 was activated with "Component C" APMA (4-aminophenylmercuric acetate) as per the SENSOLYTE kit assay protocol, for 2 hours at 37° C. Samples were prepared in duplicate.

Surrogate Enzyme Examples

Enzyme activity curves for the following surrogate enzymes were generated: Trypsin (MP Biomedicals Cat. No. 103139, commercially available from MP Biomedicals of Solon, Ohio), Trypzean (recombinant trypsin from corn, Sigma T3568 commercially available from Sigma-Aldrich Chemical Company or St. Louis, Mo.), and Thermolysin (Fluka 88303, available through Sigma-Aldrich Chemical Company). Stock solutions of the surrogate enzymes, Trypsin, Trypzean and Thermolysin were prepared in sterile DI water. Subsequent dilutions were diluted with "Component D," the assay buffer, provided in the SENSOLYTE kit, to the concentrations listed in Table 2 below. Samples were prepared in duplicate.

The MMP-9 samples and the surrogate enzyme samples (Trypsin, Trypzean and Thermolysin) were assayed according to the SENSOLYTE kit protocol. The assay was run in a Grenier black 384 well plate. After allowing the samples to incubate at room temperature conditions for 60 minutes, they were read using a Perkin Elmer 2030 Victor X5 multiwell plate reader with fluorescence monitored at Ex/Em=490 nm/535 nm; read time: 0.5 sec, 3 mm measurement height, emission aperture normal, excitation aperture normal. Assay buffer was run as an Enzyme blank

TABLE 1

Target Enzyme Activity Against MMP Substrate in SENSOLYTE 520 Assay

| Activated Pro-MMP-9 72009 (ng/mL) | Average RFU (n = 2) | Active MMP-9 PF024 (ng/mL) | Average RFU (n = 2) |
|---|---|---|---|
| 10.0 | 119497 | 10.0 | 121812 |
| 5.00 | 89559 | 5.00 | 101982 |
| 2.50 | 57111 | 2.50 | 70957 |

TABLE 1-continued

Target Enzyme Activity Against MMP Substrate in SENSOLYTE 520 Assay

| Activated Pro-MMP-9 72009 (ng/mL) | Average RFU (n = 2) | Active MMP-9 PF024 (ng/mL) | Average RFU (n = 2) |
|---|---|---|---|
| 1.25 | 34932 | 1.25 | 44153 |
| 0.625 | 16293 | 0.625 | 23194 |
| 0.313 | 7990 | 0.313 | 11941 |
| 0.156 | 4430 | 0.156 | 6341 |

TABLE 2

Surrogate Enzyme Activity Against MMP Substrate in SENSOLYTE 520 Assay

| Trypsin (µg/mL) | Ave. RFU (n = 2) | Trypzean (µg/mL) | Ave. RFU (n = 2) | Thermolysin (ng/mL) | Ave. RFU (n = 2) |
|---|---|---|---|---|---|
| 0.02 | 37543 | 20.0 | 134814 | 350 | 103032 |
| 0.01 | 25811 | 2.00 | 31611 | 35.0 | 58557 |
| 0.005 | 15310 | 0.20 | 5264 | 3.50 | 11887 |
| 0.0025 | 7993 | 0.02 | 2582 | 0.35 | 4693 |
| 0.00125 | 3082 | Enzyme Blank | 11 | — | — |
| Enzyme Blank | 7 | — | — | — | — |

Surrogate Enzyme Example

Response to Stop Solution

In the case of metalloproteinases the active site requires a metal cation for enzymatic activity. A chelating agent such as EDTA that sequesters the free metal will cause the protease to lose its enzymatic activity and potentially generate a false negative result. The surrogate investigated here, thermolysin, is therefore an ideal candidate for this class because it too requires a metal cation for activity and thus would detect a chelating interference.

The AnaSpec SENSOLYTE 520 Generic MMP Assay kit provides a stop solution, "Component E," that inactivates MMP activity. This stop solution was tested with thermolysin to demonstrate this point. The 10 ng/mL solution of Active MMP-9 (CalbioChem PF024) and the 3.5 ng/mL solution of thermolysin shown above in table 1 and table 2, respectively, were quenched with the stop solution according to the protocol provided in the SENSOLYTE kit and assayed with the same instrument and conditions performed above. The results are shown in Table 3.

TABLE 3

Thermolysin and MMP-9 Inactivation

| Active MMP-9 PF024 concentration ng/mL | Ave. RFU (n = 2) | Thermolysin concentration ng/mL | Ave. RFU (n = 2) |
|---|---|---|---|
| 10[a] | 121812 | 3.5[a] | 11887 |
| 10 + Stop Solution[b] | 1748 | 3.5 + Stop Solution[b] | 1936 |
| — | — | Background Control | 2226 |

[a] active MMP plus substrate then incubated 1 hour at room temperature prior to reading
[b] MMP plus stop solution plus substrate then incubated 1 hour at room temperature prior to reading.

Comparative Elastase Example

Elastase is another target of interest and falls into the category of serine proteases. Therefore a suitable surrogate in this class such as trypsin, chymotrypsin, or especially subtilisin (because it is a non human protease) would be subject to many of the same detriments in activity as the target.

Elastase Surrogate Enzyme Examples

A colorimetric elastase specific substrate (Calbiochem 324696) was used to test for possible surrogates to elastase. The enzymes tested were Elastase (Human neutrophil, Calbiochem 324681), subtilisin A (Sigma P5380), trypsin (MP Biomedicals 103139), and thermolysin (Sigma 88303). Stocks solutions were prepared and diluted in Tris buffer pH=7.4, commercially available from Sigma-Aldrich Chemical Company of St. Louis, Mo. Thermolysin was diluted in the assay buffer of the SENSOLYTE 520 Generic MMP Assay Kit, containing zinc. Final absorbance readings (absorbance units AU) were taken at 405 nm using a Perkin Elmer 2030 Victor X5 multiwell plate reader, after sample solutions were allowed to run for 45 minutes. Results are shown in Tables 4 and 5.

The results in Table 5 indicate that subtilisin was found to serve as a surrogate enzyme control substitute for elastase. However, trypsin and thermolysin were not found to be appropriate choices as surrogates for elastase.

TABLE 4

Elastase Enzyme Activity Colorimetric Substrate

| Elastase conc. µg/mL | Ave AU (n = 2) |
|---|---|
| 2.0 | 2.114 |
| 0.2 | 1.781 |
| 0.02 | 0.415 |

TABLE 5

Elastase Surrogate Enzyme Activity Colorimetric Substrate

| Subtlisin conc. µg/mL | Ave AU (n = 2) | Trypsin conc. µg/mL | Ave AU (n = 2) | Thermolysin conc. µg/mL | Ave AU (n = 2) |
|---|---|---|---|---|---|
| 10.0 | 0.518 | 10.0 | 0.062 | 10.0 | 0.058 |
| 1.0 | 0.121 | 1.0 | 0.059 | 1.0 | 0.060 |
| 0.1 | 0.066 | 0.1 | 0.058 | 0.1 | 0.060 |
| — | — | Blank | 0.060 | — | — |

Examples of possible targets of interest in the cysteine class are cathepsins and a suitable example surrogate in this class would be papain.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety or the portions of each that are indicated as if each were individually incorporated.

What is claimed is:

1. A method for testing efficacy of a protease enzyme assay, the method comprising:
   providing an enzyme which acts as a surrogate enzyme control for a protease enzyme;
   combining the surrogate enzyme control with an assay substrate for the protease enzyme; and
   determining a change in the assay substrate resulting from the surrogate enzyme control acting on the assay substrate;
   wherein the protease enzyme is selected from the group consisting of metalloproteinases, serine proteases, and cysteine proteases, and wherein, when the change in the assay substrate is determined to be within a predetermined range the efficacy of the assay is verified.

2. A method for conducting a protease enzyme assay, the method comprising:
   testing efficacy of the protease enzyme assay comprising:
      providing an enzyme which acts as a surrogate enzyme control for a protease enzyme;
      combining the surrogate enzyme control with an assay substrate for the protease enzyme; and
      determining a change in the assay substrate resulting from the surrogate enzyme control acting on the assay substrate; wherein, when the change in the assay substrate is determined to be within a predetermined range, the efficacy of the assay is verified; and
   determining activity of the protease enzyme in a biological sample by contacting the assay substrate with at least a portion of the biological sample;
      wherein the protease enzyme is selected from the group consisting of metalloproteinases, serine proteases, and cysteine proteases.

3. The method of claim 2, wherein the biological sample is selected from the group consisting of animal tissues, wound fluids, body fluids, saliva, tears, urine, blood serum, and blood plasma.

4. The method of claim 1, wherein the protease enzyme is a matrix metalloproteinase.

5. The method of claim 4, wherein the surrogate enzyme control is selected from the group consisting of thermolysin, porcine trypsin, bovine trypsin, and recombinant trypsin.

6. The method of claim 5, wherein the surrogate enzyme control is thermolysin.

7. The method of claim 1, wherein the protease enzyme is a serine protease.

8. The method of claim 7, wherein the surrogate enzyme is subtilisin.

9. The method of claim 1, wherein the protease enzyme is a cysteine protease.

10. The method of claim 1, wherein determining the change in the assay substrate is carried out by measuring fluorescence, ultraviolet light absorbance, or visible light absorbance.

11. The method of claim 10, wherein the assay substrate undergoes an increase in fluorescence when acted upon by the protease enzyme and by the surrogate enzyme control.

12. The method of claim 10, wherein the assay substrate undergoes a change in absorbance when acted upon by the protease enzyme and by the surrogate enzyme control.

13. The method of claim 10, wherein the change is assay substrate is visually observable or optically measurable at a binding zone of a flow device.

14. The method of claim 13, wherein the assay substrate causes the binding zone of a lateral flow device to exhibit a first color or level of color when the assay substrate is acted upon by the protease enzyme and by the surrogate enzyme control, and to exhibit a second color or level of color when the assay substrate is not acted upon by the protease enzyme and by the surrogate enzyme control.

15. A kit including:
   an enzyme which acts as a surrogate enzyme control for a protease enzyme in testing efficacy of a protease enzyme assay comprising a predetermined assay substrate for the protease enzyme;
   a reconstitution buffer; and
   an expected fluorescence range and/or an ultra violet or visible light absorbance range of the predetermined assay substrate; wherein the predetermined assay substrate at a specified concentration has a fluorescence or absorbance within the expected fluorescence or absorbance range when acted upon by the surrogate enzyme control at a specified concentration; and/or
   an expected color range or color level range of a binding zone of a flow device when contacted with the predetermined assay substrate; wherein the predetermined assay substrate causes the binding zone of the flow device to exhibit a color or level of color within the expected color range or color level range when the assay substrate is acted upon by the surrogate enzyme control at a specified concentration.

16. The kit of claim 15, wherein having a fluorescence or absorbance within the expected fluorescence or absorbance range indicates that the predetermined assay substrate is verified for use in assaying the protease enzyme.

17. The kit of claim 15, wherein the binding zone of the flow device exhibiting a color or level of color within the expected color range or color level range indicates that the predetermined assay substrate is verified for use in assaying the protease enzyme.

18. The kit of claim 15, wherein the protease enzyme is selected from the group consisting of metalloproteinases, serine proteases, and cysteine proteases.

19. The kit of claim 18, wherein the protease enzyme is a matrix metalloproteinase.

20. The kit of claim 19, wherein the surrogate enzyme control is selected from the group consisting of thermolysin, porcine trypsin, bovine trypsin, and recombinant trypsin.

21. The kit of claim 20, wherein the surrogate enzyme control is thermolysin.

22. The kit of claim 18, wherein the protease enzyme is a serine protease.

23. The kit of claim 22, wherein the surrogate enzyme is subtilisin.

24. The kit of claim 18, wherein the protease enzyme is a cysteine protease.

25. The kit of claim 15, further comprising the predetermined assay substrate.

26. The kit of claim 15, further comprising a device for assaying the protease enzyme.

27. The kit of claim 15, further comprising a sampling tool.

28. The kit of claim 15, wherein the predetermined assay substrate undergoes an increase in fluorescence when acted upon by the surrogate enzyme control.

29. The kit of claim 28, wherein the kit includes the expected fluorescence range of the predetermined assay substrate.

30. The kit of claim 15, wherein the predetermined assay substrate undergoes a change in absorbance when acted upon by the surrogate enzyme control.

31. The kit of claim 30, wherein the kit includes the expected ultra violet or visible light absorbance range of the predetermined assay substrate.

32. The kit of claim 15, wherein the predetermined assay substrate causes a binding zone of a lateral flow device to exhibit a first color or level of color when the assay substrate is acted upon by the surrogate enzyme control, and to exhibit a second color or level of color when the assay substrate is not acted upon by the surrogate enzyme control.

33. The kit of claim 32, wherein the kit includes the expected color range or color level range of the binding zone of the lateral flow device when contacted with the predetermined assay substrate acted upon by the surrogate enzyme control.

34. A method of preparing the kit of claim 15, the method comprising:
   determining the expected fluorescence or ultra violet or visible light absorbance range of the predetermined assay substrate at a specified concentration when acted upon by the surrogate enzyme control at a specified concentration; and
   providing the expected fluorescence or absorbance range for including in the kit.

35. The method of claim 34, further comprising measuring the fluorescence or absorbance of the predetermined assay substrate at the specified concentration in combination with the protease enzyme at at least one concentration; and determining if the measured fluorescence or absorbance fits a standard plot of fluorescence or absorbance of the predetermined assay substrate versus protease enzyme concentration.

36. A method of preparing the kit of claim 15, the method comprising:
   determining the expected color range or color level range of the binding zone of the lateral flow device when contacted with the predetermined assay substrate acted upon by the surrogate enzyme control at a specified concentration; and
   providing the expected color range or color level range of the binding zone of the lateral flow device for including in the kit.

* * * * *

UNITED STATES PATENT AND TRADEMARK OFFICE
CERTIFICATE OF CORRECTION

PATENT NO. : 8,349,580 B2
APPLICATION NO. : 13/394353
DATED : January 8, 2013
INVENTOR(S) : Joseph J. Stoffel et al.

It is certified that error appears in the above-identified patent and that said Letters Patent is hereby corrected as shown below:

Column 7,
Line 6, "sterptavidin" should read --streptavidin--.

Column 8,
Line 42, "hdyrate," should read --hydrate,--.
Line 46, "sequisodium," should read --sesquisodium,--.

Column 12,
Line 55, "blank" should read --blank.--.

Column 14,
Line 45, "Subtlisin" should read --Subtilisin--.

Column 15,
Line 13, "and wherein," should read --wherein,-- which should start a new paragraph.
Line 15, "range" should read --range,--.
Line 53, "ultraviolet" should read --ultra violet--.

Signed and Sealed this
Second Day of April, 2013

Teresa Stanek Rea
*Acting Director of the United States Patent and Trademark Office*